(12) United States Patent
Koyama

(10) Patent No.: US 10,168,528 B2
(45) Date of Patent: Jan. 1, 2019

(54) ENDOSCOPE

(71) Applicant: OLYMPUS CORPORATION, Tokyo (JP)

(72) Inventor: Reiji Koyama, Tachikawa (JP)

(73) Assignee: OLYMPUS CORPORATION, Tokyto (JP)

( * ) Notice: Subject to any disclaimer, the term of this patent is extended or adjusted under 35 U.S.C. 154(b) by 193 days.

(21) Appl. No.: 15/237,759

(22) Filed: Aug. 16, 2016

(65) Prior Publication Data

US 2016/0357006 A1 Dec. 8, 2016

Related U.S. Application Data

(63) Continuation of application No. PCT/JP2015/062372, filed on Apr. 23, 2015.

(30) Foreign Application Priority Data

Apr. 28, 2014 (JP) ................................. 2014-092928

(51) Int. Cl.
| | |
|---|---|
| *A61B 1/00* | (2006.01) |
| *G02B 23/24* | (2006.01) |
| *A61B 1/005* | (2006.01) |
| *A61B 1/05* | (2006.01) |

(52) U.S. Cl.
CPC ............ *G02B 23/2476* (2013.01); *A61B 1/00* (2013.01); *A61B 1/0052* (2013.01); *A61B 1/05* (2013.01)

(58) Field of Classification Search
CPC ..... G02B 23/2476; A61B 1/0052; A61B 1/05; A61B 1/00; A61B 1/0057; A61B 1/0055; A61B 1/018; A61B 1/2733; A61B 8/12; A61B 8/4466; A61B 8/445
See application file for complete search history.

(56) References Cited

U.S. PATENT DOCUMENTS

| | | | | |
|---|---|---|---|---|
| 4,905,666 | A | * | 3/1990 | Fukuda ................ A61B 1/0052 600/146 |
| 4,996,974 | A | * | 3/1991 | Ciarlei ................. A61B 1/0052 138/120 |
| 5,347,993 | A | * | 9/1994 | Tanaka ................. A61B 1/0052 600/109 |

(Continued)

FOREIGN PATENT DOCUMENTS

| | | |
|---|---|---|
| JP | 2001-046329 A | 2/2001 |
| JP | 2002-017661 A | 1/2002 |

OTHER PUBLICATIONS

International Search Report dated Aug. 11, 2015 issued in PCT/JP2015/062372.

(Continued)

*Primary Examiner* — Timothy J Neal
(74) *Attorney, Agent, or Firm* — Scully, Scott, Murphy & Presser, P.C.

(57) ABSTRACT

An endoscope includes: a bending portion; an operation portion; a frame body; a first long member; a second long member; a chain separator; a second chain cover; and a restriction surface formed on the chain separator and configured to restrict movement of the second chain cover in a direction away from the chain separator, wherein the restriction surface forms an engagement portion configured to engage the second chain cover with the chain separator.

13 Claims, 10 Drawing Sheets

(56) References Cited

U.S. PATENT DOCUMENTS

| | | | | |
|---|---|---|---|---|
| 7,780,593 B2* | 8/2010 | Ueno | ................ | A61B 1/00039 |
| | | | | 600/130 |
| 2008/0086031 A1* | 4/2008 | Mitsuya | ............... | A61B 1/0052 |
| | | | | 600/149 |
| 2010/0160730 A1* | 6/2010 | Konomura | ......... | G02B 23/2476 |
| | | | | 600/114 |
| 2015/0351609 A1* | 12/2015 | Fan | ...................... | A61B 1/0052 |
| | | | | 600/109 |

OTHER PUBLICATIONS

Japanese Office Action dated Feb. 9, 2016 issued in JP 2015-552710.

\* cited by examiner

ENDOSCOPE

CROSS REFERENCE TO RELATED APPLICATION

This application is a continuation application of PCT/JP2015/062372 filed on Apr. 23, 2015 and claims benefit of Japanese Application No. 2014-092928 filed in Japan on Apr. 28, 2014, the entire contents of which are incorporated herein by this reference.

BACKGROUND OF THE INVENTION

1. Field of the Invention

The present invention relates to an endoscope including an operation mechanism provided on an operation portion, the operation mechanism causing an action portion of an insertion portion to act.

2. Description of the Related Art

In recent years, insertion devices, such as endoscopes, have been widely used in a medical field and an industrial field.

In the endoscope used in the medical field, an elongated insertion portion can be inserted into a body cavity that is a subject to thereby observe an organ in the body cavity, and a treatment instrument inserted into an insertion channel of a treatment instrument included in the endoscope can be used as necessary to perform various treatments.

In the endoscope used in the industrial field, an elongated insertion portion of the endoscope can be inserted into an object, such as a jet engine or a pipe in a factory, to perform inspections, such as observation and various treatments of a scar, corrosion and the like of a region to be inspected in the object.

Here, a configuration in which the insertion portion of the endoscope inserted into the subject of the endoscope is provided with an action portion, such as a bending portion bendable in a plurality of directions, is well-known.

The bending portion improves progress of the insertion portion in a curve portion in a conduit and allows changing an observation direction of an observation optical system provided on a distal end portion positioned on a distal end side of the bending portion in an insertion direction (hereinafter, simply called a distal end side) in the insertion portion.

Usually, a plurality of bending pieces are linked in the insertion direction of the insertion portion, and the bending portion provided on the insertion portion of the endoscope can be bent in four vertical and horizontal directions, for example.

One of wires that are four long members inserted into the insertion portion in which a distal end in the insertion direction (hereinafter, simply called a distal end) is fixed to a bending piece positioned closest to the distal end among the bending pieces is pulled by a bending operation apparatus that is an operation mechanism of the insertion device provided on the operation portion, and the bending portion is bendable in any of the vertical and horizontal directions.

More specifically, in the bending portion, a turn knob for vertical bending operation provided on the operation portion is turned to turn a sprocket for vertical bending that is a turn body provided on the operation portion through a turning axis for vertical bending. One of an upper side chain region and a lower side chain region of a vertical bending chain member that is a long member wound around the sprocket is pulled. One of an upper side wire and a lower side wire is pulled. The upper side wire is a long member in which a proximal end in the insertion direction (hereinafter, simply called a proximal end) is connected to a distal end of the upper side chain region through a connection piece, and a distal end is connected to the bending piece. A proximal end of the lower side wire is connected to a distal end of the lower side chain region through a connection piece, and a distal end is connected to the bending piece. In this way, the bending portion is bent in one of an upper direction and a lower direction.

Furthermore, in the bending portion, a turn knob for horizontal bending operation provided on the operation portion is turned to turn a sprocket for horizontal bending that is a turn body provided on the operation portion through a turning axis for horizontal bending. One of a left side chain region and a right side chain region of a horizontal bending chain member that is a long member wound around the sprocket is pulled. One of a left side wire and a right side wire is pulled. A proximal end of the left side wire is connected to a distal end of the left side chain region through a connection piece, and a distal end is connected to the bending piece. A proximal end of the right side wire is connected to a distal end of the right side chain region through a connection piece, and a distal end is connected to the bending piece. In this way, the bending portion is bent in one of a left direction and a right direction.

The turning axis for horizontal bending on which the sprocket for horizontal bending and the turn knob for horizontal bending are fixed is pivotably supported by a frame body fixed in the operation portion and extending in the insertion direction. Note that the turning axis for vertical bending on which the turn knob for vertical bending is fixed is covered by a circumference of the turning axis for horizontal bending.

The frame body is formed in a thin plate shape from a metallic member. The frame body functions as a member configured to position various components provided in the operation portion and resist tensile force acting back and forth in the insertion direction of the operation portion when a grasping portion is fixed to an operation portion main body of the operation portion. The frame body also functions as a so-called bottom board in which the proximal end of the insertion portion is fixed on the distal end side.

On one surface of the frame body, a first surface of a chain separator that is a guide member with a cross shape in cross section configured to separate the upper side chain region, the lower side chain region, the left side chain region, and the right side chain region to avoid interference with each other and guide the regions back and forth in the insertion direction is also fixed by screws or the like.

Note that the chain separator is formed in a cross shape in cross section, and four insertion paths of the respective chain regions are formed on the chain separator. The respective chain regions are individually inserted into the insertion paths, and the chain separator prevents the interference among the respective chain regions.

In a state that the respective chain regions are inserted into the respective insertion paths, the vertical bending chain member and the horizontal bending chain member are positioned to overlap in a height direction in which the chain separator overlaps with the frame body.

More specifically, the upper side chain region and the right side chain region are positioned to overlap, and the lower side chain region and the left side chain region are positioned to overlap. That is, one of the upper side chain region and the lower side chain region and the left side chain region and the right side chain region comes into contact with one surface of the frame body.

A chain cover that is a plate-like member is placed on a second surface on an opposite side of the first surface in the height direction of the chain separator. The chain cover guides the back and forth movement of the upper side chain region and the lower side chain region in the insertion direction and prevents the upper side chain region and the lower side chain region from dropping out from the insertion path in the height direction when, for example, the left side chain region and the right side chain region come into touch with one surface of the frame body, and the upper side chain region and the lower side chain region are positioned closer to the second surface than the left side chain region and the right side chain region in the height direction.

Note that when a plurality of holes and the like are formed on the frame body, the left side chain region and the right side chain region moving back and forth in the insertion direction may be caught by the holes and the like. Therefore, to guide the back and forth movement of the left side chain region and the right side chain region in the insertion direction, a chain cover may also be provided and placed between the first surface of the chain separator and the frame body, in addition to the chain cover placed on the second surface.

Note that the chain cover placed on the second surface of the chain separator will be called a second chain cover, and the chain cover positioned and placed between the frame body and the chain separator will be called a first chain cover.

In Japanese Patent Application Laid-Open Publication No. 2001-46329, a configuration of fixing the second chain cover to the frame body by screws is disclosed.

More specifically, Japanese Patent Application Laid-Open Publication No. 2001-46329 discloses a configuration, in which through holes into which screws are inserted are provided at intermediate positions of the chain separator and the second chain cover in the insertion direction, wherein the positions do not overlap with the respective insertion paths, and the positions protrude outside in a width direction orthogonal to the insertion direction and the height direction. Screw holes are provided on the frame body, and screws inserted into the respective through holes are screwed to the screw holes of the frame body to thereby fix the second chain cover to the frame body through the chain separator.

Note that a configuration of providing a spacer configured to fill a gap between the through holes of the chain separator and the through holes of the second chain cover in the height direction is also well-known.

According to the configurations, not only the second chain cover can be surely fixed by screws, but the fixation of the second chain cover by screws can also prevent deflection of the second chain cover formed from a thin-plate resin caused by weights of the upper side chain region and the lower side chain region downward in a direction of gravity, even when, for example, the second chain cover is formed from a thin-plate resin, and the second chain cover is positioned on a lower side in the direction of gravity due to a change in posture of the operation portion.

Note that the fixation configuration of the second chain cover described above may also be used for the fixation of the first chain cover. That is, through holes into which screws are inserted may be provided on the first chain cover.

SUMMARY OF THE INVENTION

An aspect of the present invention provides an endoscope including: a bendable bending portion provided on an insertion portion inserted into a subject; an operation portion consecutively connected to a proximal end of the insertion portion and operated by an operator to bend the bending portion; a frame body fixed in the operation portion and configured to position members in the operation portion; a first long member connected to the bending portion, inserted into the insertion portion and the operation portion, and moved by operating the operation portion; a second long member connected to the bending portion, inserted into the insertion portion and the operation portion, and moved by operating the operation portion; a guide member configured to separately arrange the first long member and the second long member and guide the movement of the first long member along with the frame body; a first plate-like member arranged to face the guide member to guide the second long member along with the guide member; and an engagement portion formed on the guide member and including a restriction surface for restricting movement of the first plate-like member in a direction away from the guide member, the restriction surface causing the first plate-like member to engage with the guide member.

DETAILED DESCRIPTION OF THE PREFERRED EMBODIMENT(S)

Hereinafter, an embodiment of the present invention will be described with reference to the drawings. Note that the drawings are schematic drawings, and a relationship between a thickness and a width of each member, a ratio of the thickness of respective members, and the like are different from reality. It is obvious that the relationship and the ratio of dimensions between the drawings are different in some parts of the drawings.

Figure 1:
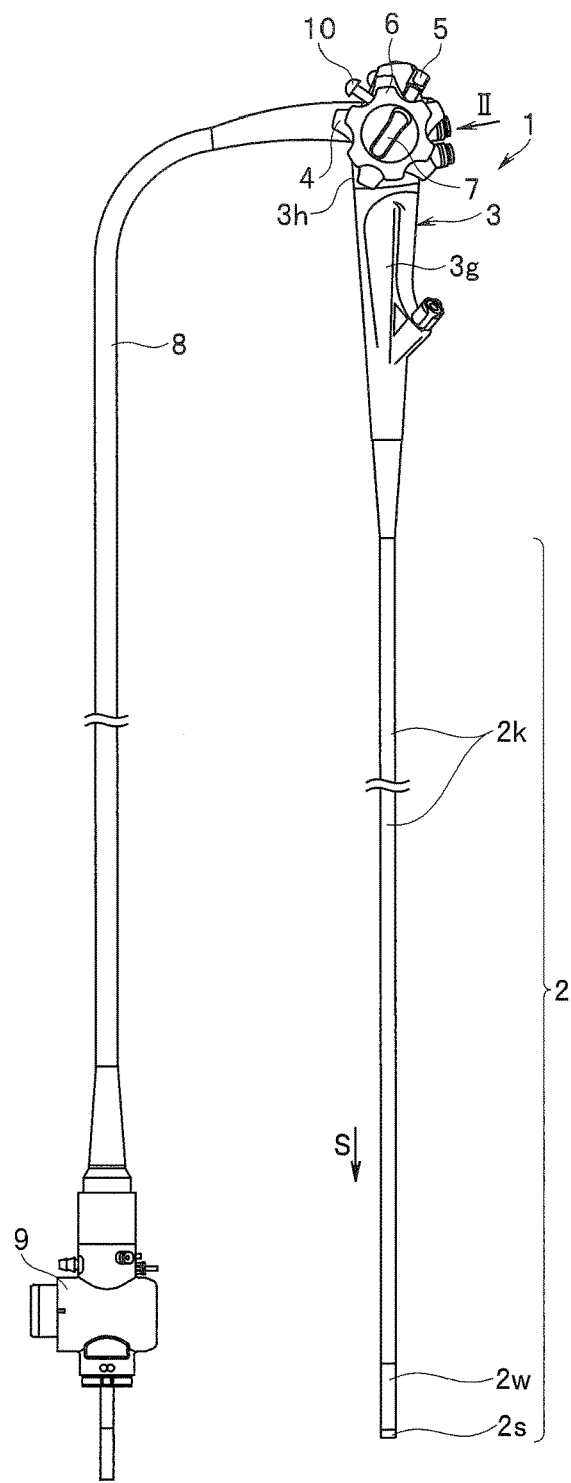
FIG. 1 is a diagram showing an appearance of an endoscope according to the present embodiment.

FIG. 1 is a diagram showing an appearance of an endoscope according to the present embodiment.

As shown in FIG. 1, main components of an endoscope 1 include: an insertion portion 2 inserted into a subject; an operation portion 3 consecutively connected to a proximal end of the insertion portion 2; a universal cord 8 extended from the operation portion 3; and a connector 9 provided on an extended end of the universal cord 8. Note that the endoscope 1 is electrically connected to an external apparatus, such as a control apparatus and a lighting apparatus, through the connector 9.

Main components of the insertion portion 2 include: a long flexible tube portion 2k extending in an insertion direction S of the insertion portion 2; a bending portion 2w that is an action portion positioned in front of the flexible tube portion 2k in the insertion direction S (hereinafter, simply referred to as in front of); and a distal end portion 2s positioned in front of the bending portion 2w.

An image pickup unit not shown configured to pick up an image inside of the subject, a lighting unit not shown configured to supply illumination light into the subject, and the like are provided in the distal end portion 2s.

Turn knobs 4 and 6 for bending operation described later provided on the operation portion 3 allow the bending portion 2w to bend in, for example, four vertical and horizontal directions.

Main components of the operation portion 3 include: a grasping portion 3g grasped by an operator; and an operation portion main body 3h connected to a proximal end of the grasping portion 3g and operated by the operator, wherein the universal cord 8 extends from the operation portion main body 3h.

The operation portion main body 3h is provided with: the turn knob 4 for vertical bending operation configured to bend the bending portion 2w in the vertical direction; and the turn knob 6 for horizontal bending operation configured to bend the bending portion 2w in the horizontal direction. The operation portion main body 3h is also provided with: a fixation lever 5 configured to fix a turning position of the turn knob 4; a fixation knob 7 configured to fix a turning position of the turn knob 6; and a zoom lever 10 of the image pickup unit provided in the distal end portion 2s.

Note that the turn knob 4, the fixation lever 5, the turn knob 6, and the fixation knob 7, along with other members described later provided in the operation portion 3, form a bending operation apparatus 100 (see FIG. 2) that is an operation mechanism of an insertion device described later according to the present embodiment.

Next, a configuration of the bending operation apparatus 100 of the endoscope provided on the operation portion 3 will be described with reference to FIGS. 2 to 9.

Figure 2:
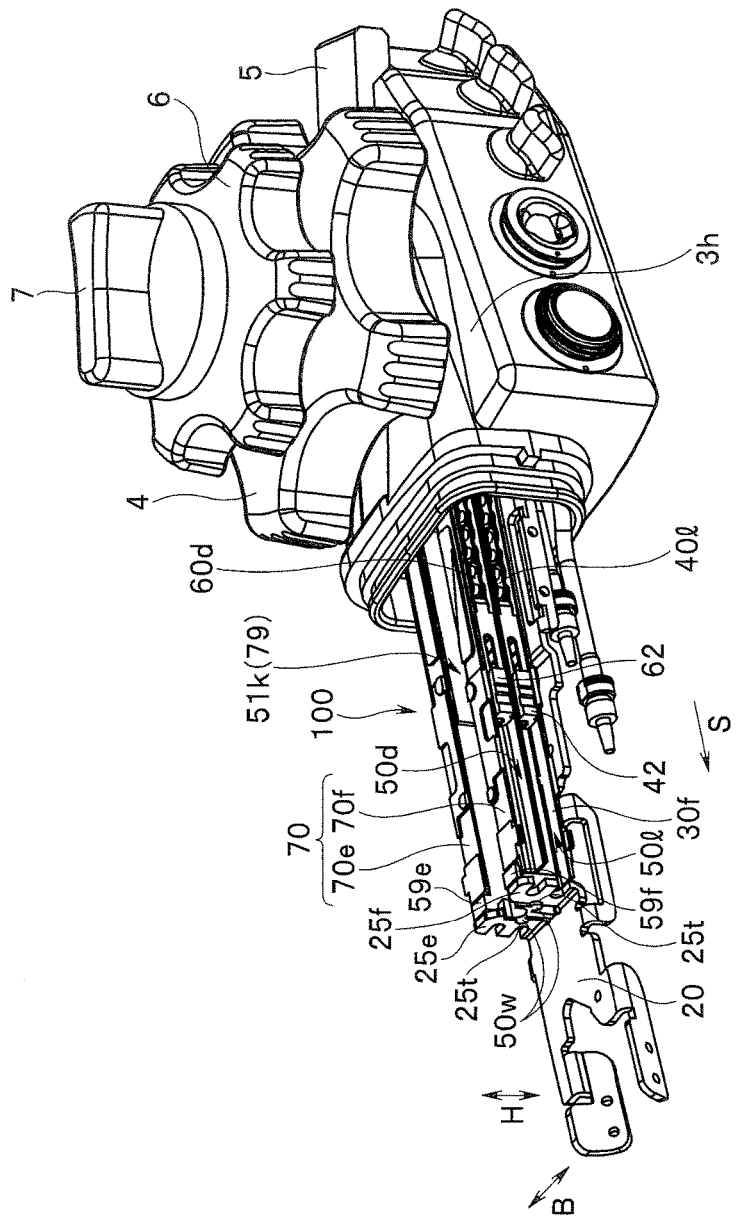
FIG. 2 is a perspective view, in which a grasping portion is excluded from an operation portion of the endoscope to expose and illustrate part of a bending operation apparatus in the operation portion along with tubes as viewed in a direction II of FIG. 1.
Figure 3:
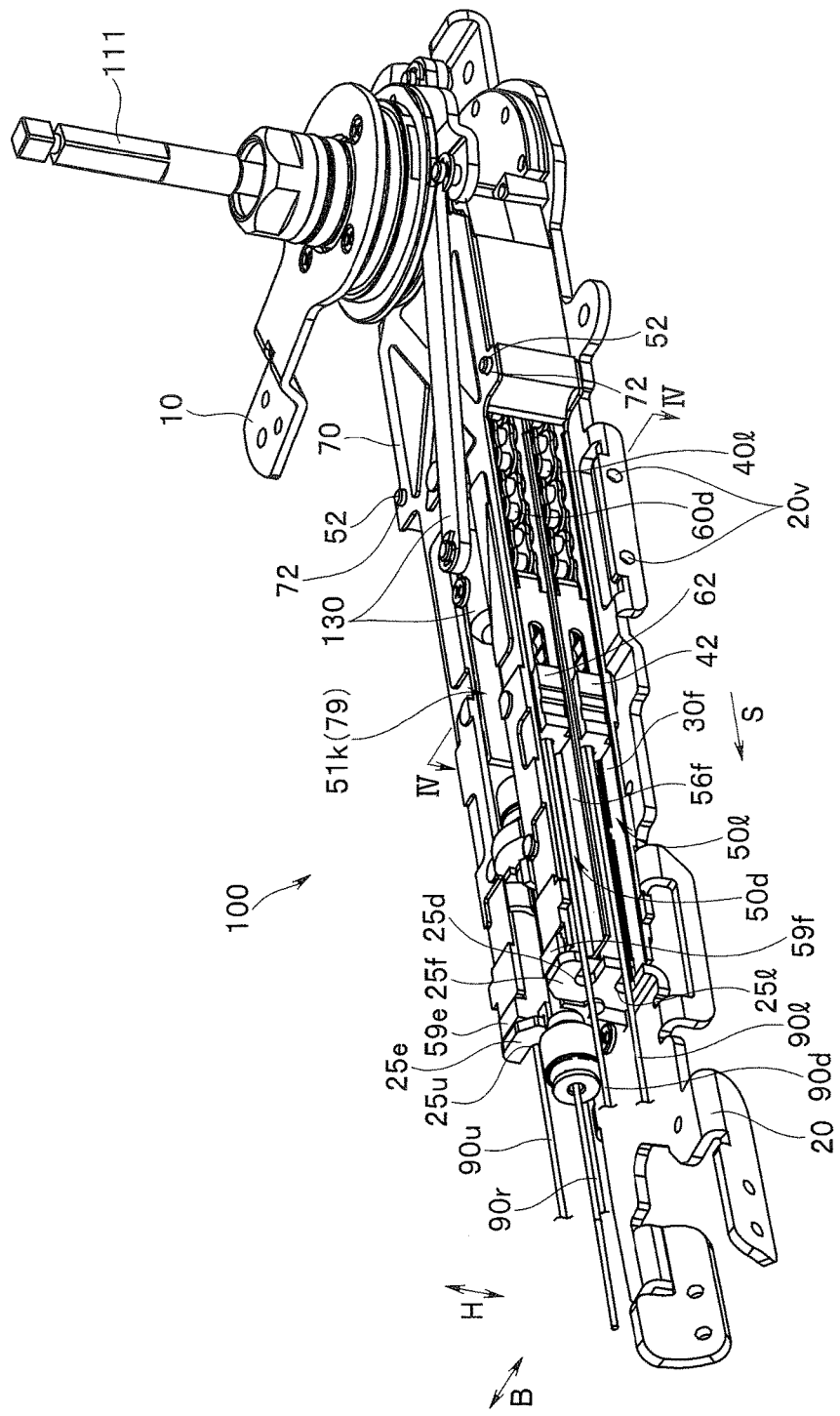
FIG. 3 is a perspective view of part of the bending operation apparatus illustrated by excluding an operation portion main body, turn knobs, and a fixation lever from the operation portion of FIG. 2.

FIG. 2 is a perspective view, in which the grasping portion is excluded from the operation portion of the endoscope to expose and illustrate part of the bending operation apparatus in the operation portion along with tubes as viewed in a direction II of FIG. 1. FIG. 3 is a perspective view of part of the bending operation apparatus illustrated by excluding the operation portion main body, the turn knobs, and the fixation lever from the operation portion of FIG. 2.

Note that a link mechanism of a wire and the zoom lever is not illustrated in FIG. 2. A turning axis for vertical bending is not illustrated in FIG. 3.

Figure 4:
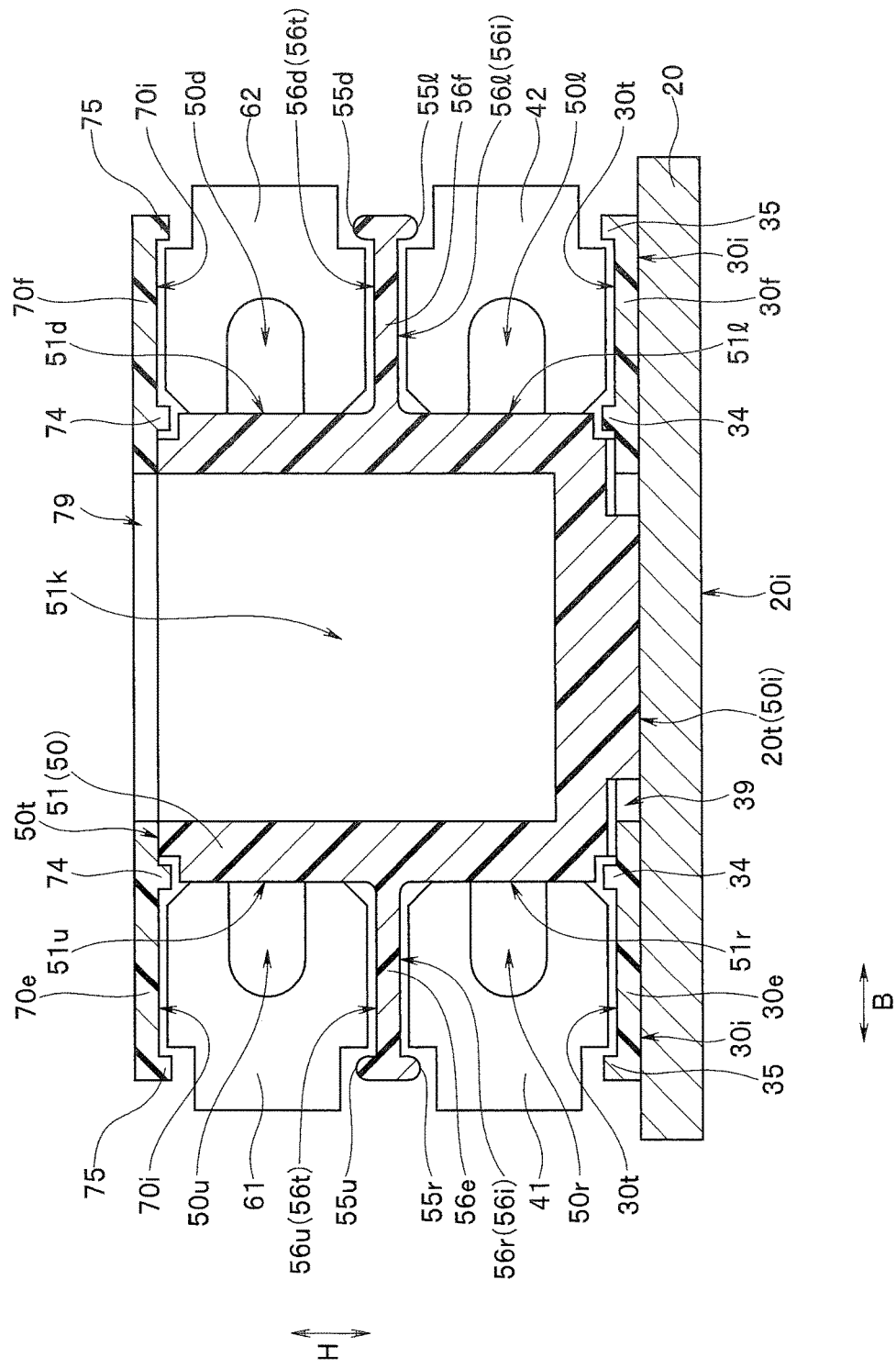
FIG. 4 is a diagram schematically showing, along with respective connection pieces, a cross section of a chain separator, a first chain cover, and a second chain cover along a line IV-IV in FIG. 3.
Figure 5:
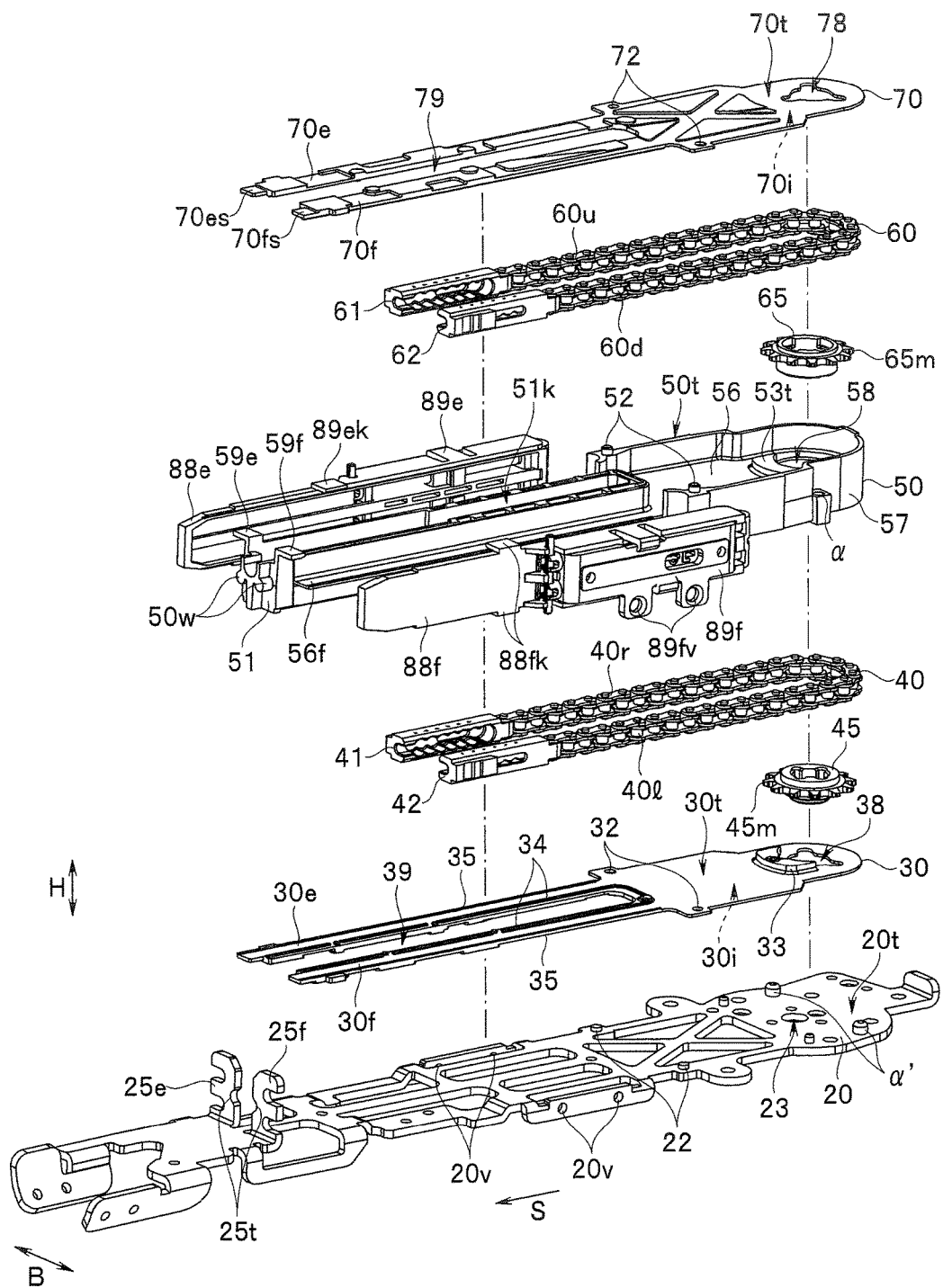
FIG. 5 is an exploded perspective view of part of the bending operation apparatus of FIG. 2.

FIG. 4 is a diagram schematically showing, along with respective connection pieces, a cross section of a chain separator, a first chain cover, and a second chain cover along a line IV-IV in FIG. 3. FIG. 5 is an exploded perspective view of part of the bending operation apparatus of FIG. 2, showing a state before assembly of the chain separator and a frame body described later.

Figure 6:
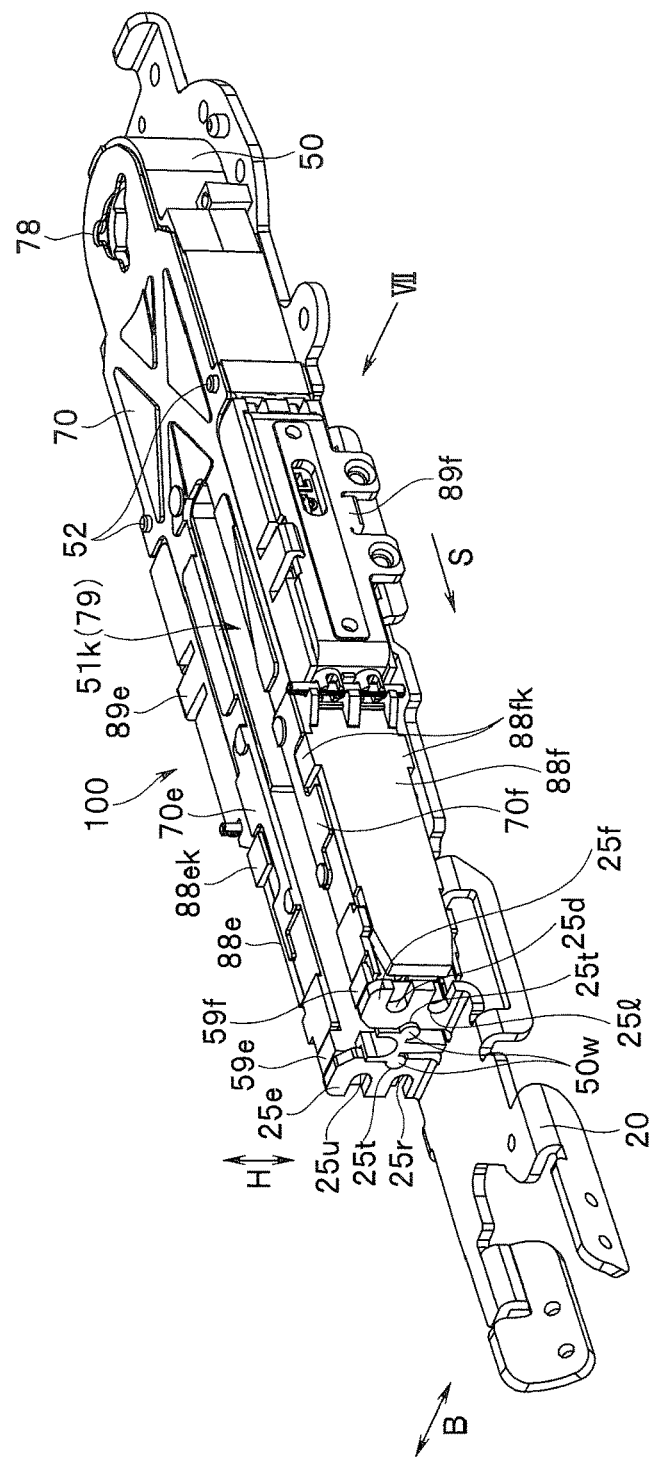
FIG. 6 is a perspective view of the bending operation apparatus showing a state in which the first chain cover, the chain separator, the second chain cover, guide blocks, a vertical bending sprocket, and a horizontal bending sprocket are assembled on a frame body of FIG. 5.

FIG. 6 is a perspective view of the bending operation apparatus showing a state in which the first chain cover, the chain separator, the second chain cover, guide blocks, a vertical bending sprocket, and a horizontal bending sprocket are assembled on the frame body of FIG. 5.

Figure 7:
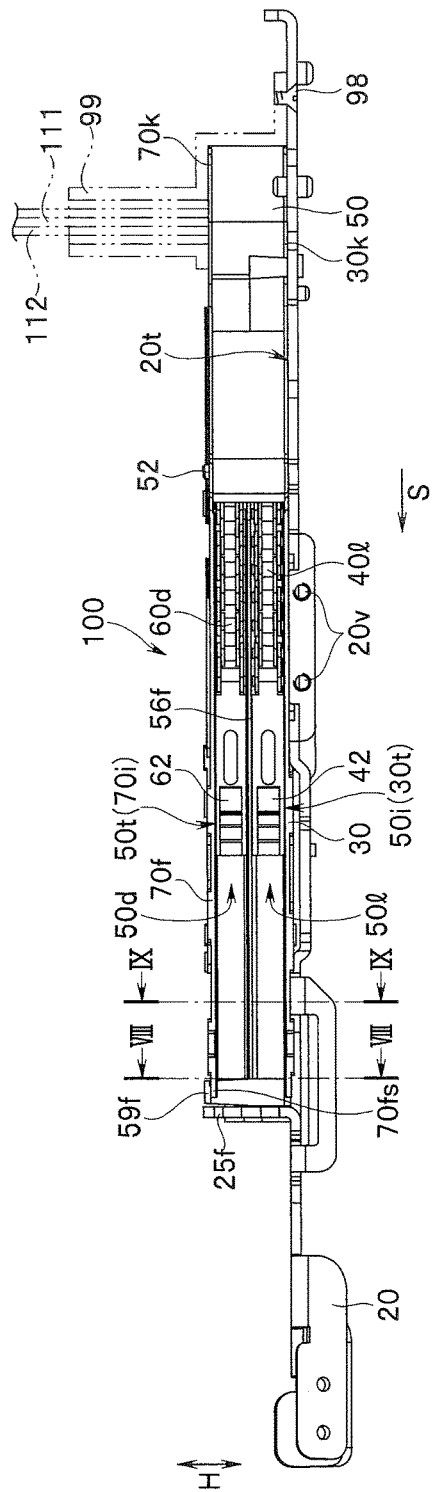
FIG. 7 is a side view, in which the bending operation apparatus of FIG. 6 is viewed in a direction VII in FIG. 6, the guide blocks are removed, and a position for assembling a frame shaft in the state of FIG. 6 is indicated.
Figure 8:
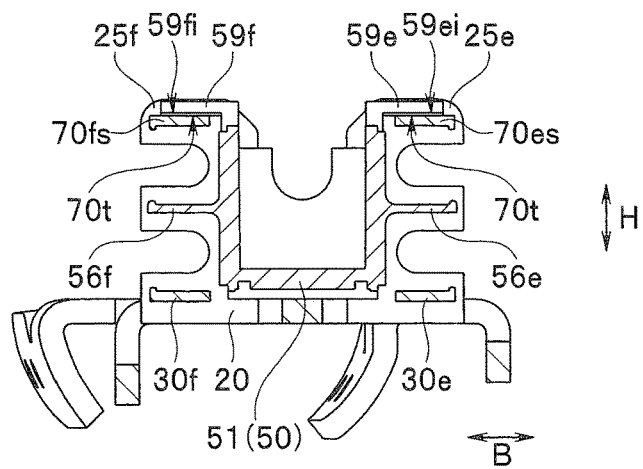
FIG. 8 is a partial sectional view of the bending operation apparatus along a line VIII-VIII in FIG. 7.
Figure 9:
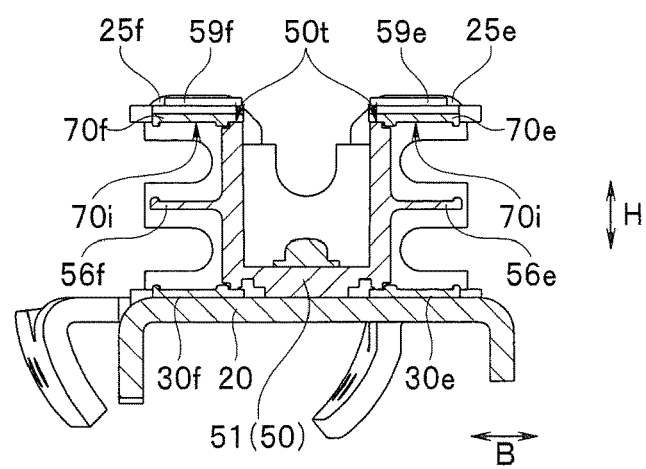
FIG. 9 is a partial sectional view of the bending operation apparatus along a line IX-IX in FIG. 7.

FIG. 7 is a side view, in which the bending operation apparatus of FIG. 6 is viewed in a direction VII in FIG. 6, the guide blocks are removed, and a position of assembling a frame shaft in the state of FIG. 6 is indicated. FIG. 8 is a partial sectional view of the bending operation apparatus along a line VIII-VIII in FIG. 7, and FIG. 9 is a partial sectional view of the bending operation apparatus along a line IX-IX in FIG. 7.

As shown in FIG. 2, the bending operation apparatus 100 includes the turn knobs 4 and 6, the fixation lever 5, and the fixation knob 7 positioned outside of the operation portion 3.

As shown in FIGS. 5 and 7, the bending operation apparatus 100 includes, in the operation portion 3: a turning axis 112 for vertical bending, in which the turn knob 4 is fixed on one end, and the turning axis 112 is pivotable along with the turn knob 4; and a sprocket 65 for vertical bending that is a turn body fixed to the other end of the turning axis 112 and pivotable along with the turning axis 112.

As shown in FIGS. 3 and 5, the bending operation apparatus 100 further includes, in the operation portion 3: a turning axis 111 (see FIG. 3) for horizontal bending, in which the turn knob 6 is fixed to one end, and the turning axis 111 is pivotable along with the turn knob 6; and a sprocket 45 (see FIG. 5) for horizontal bending that is a turn body fixed to the other end of the turning axis 111 and pivotable along with the turning axis 111.

As shown in FIGS. 2 to 9, the bending operation apparatus 100 further includes, in the operation portion 3: a frame body 20; a first chain cover 30 that is a second plate-like member; a chain separator 50 that is a guide member; a second chain cover 70 that is a first plate-like member; a horizontal bending chain member 40 that is a first long member wound around the sprocket 45; a vertical bending chain member 60 that is a second long member wound around the sprocket 65.

As shown in FIG. 5, the frame body 20 is formed in a thin plate shape from, for example, a metallic material. Inside of the operation portion 3, the frame body 20 is fixed in a state that a surface 20t of the frame body 20 on which the first chain cover 30 comes into contact extends in the insertion direction S so as to face the turn knobs 4 and 6.

The frame body 20 is provided with a plurality of holes penetrating through the frame body 20 in a height direction H connecting a first surface 50i and a second surface 50t of the chain separator 50 and a plurality of positioning holes for fixing or positioning various members on the frame body 20.

The surface 20t of the frame body 20 is provided with, for example, protrusions α' for positioning the chain separator 50. Note that the formation of the plurality of holes on the frame body 20 lightens the frame body 20 formed from the metallic material.

A distal end side of the frame body 20 is a region where the proximal end of the insertion portion 2 is fixed. A support hole 23 penetrating in the height direction H for pivotably supporting the turning axis 111 (see FIG. 3) is formed on a proximal end side of the frame body 20 in the insertion direction S (hereinafter, simply called a proximal end side).

As shown in FIGS. 3, 5, and 7, at intermediate positions of the frame body 20 in the insertion direction S, screw holes 20v for fixing bearing plates 89f and 89e described later by screws are formed on both side surfaces in a width direction B orthogonal to the insertion direction S and the height direction H of the frame body 20.

At one location of the inter intermediate position on the surface 20t of the frame body 20 in the insertion direction S on which the first chain cover 30 comes into contact, such as at a position closer to the proximal end side than the screw holes 20v, two positioning protrusions 22 fitted into two positioning holes 32 described later of the first chain cover 30 to position the first chain cover 30 in the insertion direction S and the width direction B are provided to rise up in the height direction H from the surface 20t, for example.

As shown in FIGS. 2, 3, and 5 to 9, two support members 25e and 25f configured to hold a distal end of the chain separator 50 are provided on a distal end side of the surface 20t, each of the two support members 25e and 25f rising up in the height direction H from the surface 20t at a predetermined interval in the width direction B.

Holes α are provided on a proximal end side of the chain separator 50 and are engaged with the protrusions α' provided on a proximal end side of the surface 20t. According to the configuration, the chain separator 50 is positioned relative to the frame body 20 by the holes α and the protrusions α' on a proximal end side of the operation portion 3 as shown in FIG. 5. The proximal end side of the chain separator 50 is sandwiched by a frame shaft 99 and the frame body 20 along with the chain cover 30 to prevent the chain separator 50 from dropping out from the frame body 20.

In this way, a dimension of the chain separator 50 with a coefficient of linear expansion significantly different from that of the frame body 20 is allowed to change in some degree in the direction S, and possibility of generation of unintended stress can be reduced. Other components, such as screws, for fixing the frame body 20 and the chain separator 50 can also be reduced.

As shown in FIGS. 3 and 6, penetration portions 25r and 25u through which wires 90r and 90u penetrate in the insertion direction S are formed on the support member 25e and overlap in the height direction H. Penetration portions 25l and 25d through which wires 90l and 90d penetrate in the insertion direction S are formed on the support member 25f and overlap in the height direction H.

As shown in FIGS. 2 and 6, engagement grooves 25t for engaging engagement protrusions 50w described later provided on the distal end of the chain separator 50 are formed on respective opposed surfaces of the respective support members 25e and 25f in the width direction B.

The first chain cover 30 is formed in a thin plate shape from a highly lubricant resin, such as polyacetal (POM), and is positioned and placed between the frame body 20 and the first surface 50i of the chain separator 50 described later facing the frame body 20 in the height direction H.

Note that the first chain cover 30 is formed from a resin to lighten the first chain cover 30 and to form the first chain cover 30 into various shapes inexpensively.

As shown in FIG. 7, a proximal end 30k is pressed against the surface 20t by the frame shaft 99 covering circumferences of the other end side of the turning axis 112 for vertical bending and the other end side of the turning axis 111 for horizontal bending to fix the first chain cover 30 to the frame body 20.

Note that a contact region of the frame shaft 99 relative to the surface 20t is fixed to the frame body 20 by a screw 98.

The two positioning protrusions 22 of the frame body 20 are fitted into the two positioning holes 32 formed to penetrate through the first chain cover 30 in the height direction H, and the first chain cover 30 is positioned relative to the frame body 20 in the insertion direction S and the width direction B.

Here, the first chain cover 30 is formed from a resin, and the frame body 20 is formed from a metallic material as described above. Therefore, the coefficients of linear expansion of the first chain cover 30 and the frame body 20 are significantly different.

The endoscope 1 may be placed under a high-temperature high-humidity environment and a low-temperature low-humidity environment during cleaning, disinfection, and sterilization, and in this case, the coefficients of linear expansion of the first chain cover 30 and the frame body 20 are different. Therefore, amounts of deformation are different under the high-temperature high-humidity environment and under the low-temperature low-humidity environment, and as a result, the first chain cover 30 is significantly deformed under the high-temperature high-humidity environment and under the low-temperature low-humidity environment after the assembly.

If the first chain cover 30 is significantly deformed, slidability of the horizontal bending chain member 40 decreases because a surface 30t of the first chain cover 30 is a surface on which the horizontal bending chain member 40 slides and moves back and forth in the insertion direction S as described later, and a bending operation of the bending portion 2w is adversely affected.

Even a slight deformation of the first chain cover 30 may generate internal stress in the first chain cover 30, and for example, when a cleaning/disinfecting apparatus is used to clean and disinfect the endoscope 1, the first chain cover 30 is placed under an environment in which a high temperature and a low temperature are repeated. In this case, the internal stress generated in the first chain cover 30 may reduce a product life of the first chain cover 30.

Note that the problem can be ignored when the first chain cover 30 and the frame body 20 are formed by a same material.

Therefore, in the present embodiment, the positioning of the first chain cover 30 relative to the frame body 20 in the insertion direction S and the width direction B is performed only by fitting the two positioning protrusions 22 provided at only one location in the intermediate position of the frame body 20 in the insertion direction S, into the two positioning holes 32 of the first chain cover 30.

Note that other than the fact that the two positioning protrusions 22 are fitted into the two positioning holes 32, and the proximal end 30k is fixed, the first chain cover 30 is just placed such that a surface 30i described later comes into contact with the surface 20t of the frame body 20.

As a result, even if the amounts of deformation are different, since the first chain cover 30 and the frame body 20 are not tightly joined and fixed, the internal stress generated in the first chain cover 30 due to the fixation with the frame body 20 can be small, and a large deformation of the first chain cover 30 can be eliminated.

Note that the foregoing is the same when the first chain cover 30 is formed from a resin, the chain separator 50 is formed from metal, and positioning protrusions not shown provided on the first surface 50*i* described later of the chain separator 50 are fitted into positioning holes not shown formed on the first chain cover 30 to thereby position the first chain cover 30 relative to the chain separator 50 in the insertion direction S and the width direction B.

Returning to FIG. 5, a slit 39 is formed in the insertion direction S on a center portion in the width direction B of a front half portion of the first chain cover 30 in the insertion direction S, and the front half portion is formed into two parts.

Note that one side of the front half portion of the first chain cover 30 in the width direction B will be called one side 30*e*, and the other side will be called the other side 30*f*.

As shown in FIGS. 4 and 5, the surface 30*i* of the first chain cover 30 closer to the frame body 20 is a surface coming into contact with the surface 20*t* of the frame body 20.

As shown in FIG. 5, a holding hole 38 of the sprocket 45 penetrating in the height direction H is formed on a proximal end side of the first chain cover 30. The sprocket 45 is pivotably held relative to the holding hole 38 such that a winding portion 45*m* is exposed toward the surface 30*t* of the first chain cover 30.

The surface 30*t* facing the surface 30*i* of the first chain cover 30 is a surface guiding back and forth movement of the horizontal bending chain member 40 in the insertion direction S. In other words, the first chain cover 30 guides the movement of the horizontal bending chain member 40 along with the chain separator 50. Since the first chain cover is fixed to the frame body 20, it can be rephrased that the horizontal bending chain member 40 is guided by the frame body 20 and the chain separator 50.

More specifically, the horizontal bending chain member 40 is wound around the winding portion 45*m*, and an intermediate position is wound around the winding portion 45*m*. In this way, the horizontal bending chain member 40 is formed in a U shape with one side 40*r* and the other side 40*l*.

As shown in FIGS. 3 and 5, a proximal end of the wire 90*r* for right side bending is connected to a distal end of the one side 40*r* through a connection piece 41, wherein the wire 90*r* is a first long member with a distal end fixed to a distal end of the bending portion 2*w*. A proximal end of the wire 90*l* for left side bending is connected to a distal end of the other side 40*l* through a connection piece 42, wherein the wire 90*l* is a first long member with a distal end fixed to the distal end of the bending portion 2*w*.

Note that the wire 90*r* penetrates through the penetration portion 25*r* of the support member 25*e* in the insertion direction S, and the wire 90*l* penetrates through the penetration portion 25*l* of the support member 25*f* in the insertion direction S.

That is, the first long member is inserted into the insertion portion 2 and the operation portion 3, and the intermediate position of the horizontal bending chain member 40 is wound around the winding portion 45*m* in the insertion portion 2 and the operation portion 3. In this way, the first long member includes the wire 90*r* and the one side 40*r* of the horizontal bending chain member 40 that are one side of the first long member and the wire 90*l* and the other side 40*l* of the horizontal bending chain member 40 that are the other side of the first long member, and the first long member is provided in a U shape.

As a result, the bending portion 2*w* is bent in a right direction when the turn knob 6 is turned, the sprocket 45 is turned through the turning axis 111, the wire 90*r* and the one side 40*r* are pulled, and the wire 90*l* and the other side 40*l* are relaxed. The bending portion 2*w* is bent in a left direction when the wire 90*r* and the one side 40*r* are relaxed, and the wire 90*l* and the other side 40*l* are pulled.

In this case, the horizontal bending chain member 40 is slidable relative to the surface 30*t* of the first chain cover 30. This prevents the horizontal bending chain member 40 from being caught by the plurality of holes formed on the frame body 20.

Note that as shown in FIG. 4, on the surface 30*t* of the one side 30*e* of the first chain cover 30, the one side 40*r* of the horizontal bending chain member 40 can slide back and forth in the insertion direction S in an insertion path 50*r* described later. On the surface 30*t* of the other side 30*f*, the other side 40*l* of the horizontal bending chain member 40 can slide back and forth in the insertion direction S in an insertion path 50*l* described later.

Note that the surface 30*t* of the one side 30*e* is exposed to the insertion path 50*r*, and this will be described later. The surface 30*t* of the other side 30*f* is exposed to the insertion path 50*l*, and this will be described later.

As shown in FIG. 4, on the surfaces 30*t* of the one side 30*e* and the other side 30*f* of the first chain cover 30, ribs 34 and 35 are formed in the insertion direction S on end portions parallel in the insertion direction S, or more specifically, on end portions surrounding the slit 39 and end portions outside in the width direction B.

The rib 34 is formed in a U shape. The rib 34 guides the one side 40*r* of the horizontal bending chain member 40 to prevent the one side 40*r* from dropping out from the surface 30*t* of the one side 30*e* toward the slit 39 and guides the other side 40*l* of the horizontal bending chain member 40 back and forth in the insertion direction S to prevent the other side 40*l* from dropping out from the surface 30*t* of the other side 30*f* toward the slit 39.

The rib 35 guides the one side 40*r* of the horizontal bending chain member 40 to prevent the one side 40*r* from dropping out from the surface 30*t* of the one side 30*e* to the outside in the width direction B and guides the other side 40*l* of the horizontal bending chain member 40 back and forth in the insertion direction S to prevent the other side 40*l* from dropping out from the surface 30*t* of the other side 30*f* to the outside in the width direction B.

That is, the ribs 34 and 35 guide the one side 40*r* and the other side 40*l* back and forth in the insertion direction S to prevent the one side 40*r* and the other side 40*l*, or more specifically, at least the connection piece 41 and the connection piece 42, from dropping out from the respective insertion paths 50*r* and 50*l*.

On the surface 30*t* of the first chain cover 30, an alignment convex portion 33 is provided in front of and near the holding hole 38. The alignment convex portion 33 guides the one side 40*r* of the horizontal bending chain member 40 to the insertion path 50*r*, that is, the surface 30*t* of the one side 30*e* of the first chain cover 30, and guides the other side 40*l* of the horizontal bending chain member 40 to the insertion path 50*l*, that is, the surface 30*t* of the other side 30*f* of the first chain cover 30. The alignment convex portion 33 also prevents interference of the one side 40*r* and the other side 40*l* caused by looseness of one of the one side 40*r* and the other side 40*l*.

The first chain cover 30 is placed on the first surface 50*i* described later of the chain separator 50 to cover the first surface 50*i* to thereby prevent the horizontal bending chain member 40, the connection piece 41, and the connection piece 42 from dropping out from the chain separator 50 toward the frame body 20 in the height direction H.

Note that as described above, the first chain cover 30 may further include two positioning holes in addition to the two positioning holes 32. Two positioning protrusions not shown formed only at one location in the intermediate position in the insertion direction S on the first surface 50i of the chain separator 50 may be fitted into the two positioning holes to thereby position the first chain cover 30 relative to the chain separator 50 in the insertion direction S and the width direction B.

Shapes of the surface 30i and the surface 30t of the first chain cover 30 are different, and the operator does not make a mistake in the direction of attaching the first chain cover 30 during the assembly.

The second chain cover 70 is formed in a thin plate shape from a highly lubricant resin, such as polyacetal (POM), and is placed to come into contact with the second surface 50t described later on the opposite side of the first surface 50i described later of the chain separator 50 in the height direction H.

Note that like the first chain cover 30, the second chain cover 70 is formed from a resin to lighten the second chain cover 70 and to form the second chain cover 70 into various shapes inexpensively.

As shown in FIG. 7, the second chain cover 70 is fixed by the frame shaft 99 pressing a proximal end 70k against the surface 20t along with the proximal end of the chain separator 50 and the proximal end 30k of the first chain cover 30 with respect to the frame body 20.

As shown in FIGS. 2, 3, 5, and 6, a distal end 70es of one side 70e and a distal end 70fs of the other side 70f described later of the second chain cover 70 are engaged with engagement portions 59e and 59f described later of the chain separator 50, respectively.

On the second surface 50t described later of the chain separator 50, the two positioning protrusions 52 formed only at one location in the intermediate position in the insertion direction S are fitted into two positioning holes 72 formed to penetrate through the second chain cover 70 in the height direction H, and the second chain cover 70 is positioned relative to the chain separator 50 in the insertion direction S and the width direction B.

As shown in FIGS. 2, 3, 5, and 6, a slit 79 is formed in the insertion direction S on a center portion in the width direction B of a front half portion of the second chain cover 70 in the insertion direction S, and the front half portion is formed into two parts.

Note that one side of the front half portion of the second chain cover 70 in the width direction B will be called the one side 70e, and the other side will be called the other side 70f.

As shown in FIG. 3, a surface 70t of the second chain cover 70 on an opposite side of the chain separator 50 is a surface facing a link mechanism 130 of the zoom lever 10.

As shown in FIG. 5, a holding hole 78 of the sprocket 65 penetrating in the height direction H is formed on a proximal end side of the second chain cover 70. The sprocket 65 is pivotably held relative to the holding hole 78 such that a winding portion 65m is exposed toward a surface 70i described later.

The surface 70i facing the surface 70t of the second chain cover 70 is a surface guiding the vertical bending chain member 60. In other words, the second chain cover 70 guides the vertical bending chain member 60 along with the chain separator 50.

More specifically, the vertical bending chain member 60 is wound around the winding portion 65m, and an intermediate position is wound around the winding portion 65m. In this way, the vertical bending chain member 60 is formed in a U shape with one side 60u and the other side 60d.

As shown in FIGS. 3 and 5, a proximal end of the wire 90u for upper side bending is connected to a distal end of the one side 60u through a connection piece 61, wherein the wire 90u is a second long member with a distal end fixed to the distal end of the bending portion 2w. A proximal end of the wire 90d for lower side bending is connected to a distal end of the other side 60d through a connection piece 62, wherein the wire 90d is a second long member with a distal end fixed to the distal end of the bending portion 2w.

Note that the wire 90u penetrates through the penetration portion 25u of the support member 25e in the insertion direction S, and the wire 90d penetrates through the penetration portion 25d of the support member 25f in the insertion direction S.

That is, the second long member is inserted into the insertion portion 2 and the operation portion 3, and the intermediate position of the vertical bending chain member 60 is wound around the winding portion 65m in the insertion portion 2 and the operation portion 3. In this way, the second long member includes the wire 90u and the one side 60u of the vertical bending chain member 60 that are one side of the second long member and the wire 90d and the other side 60d of the vertical bending chain member 60 that are the other side of the second long member, and the second long member is provided in a U shape.

As a result, the bending portion 2w is bent in an upper direction when the turn knob 4 is turned, the sprocket 65 is turned through the turning axis 112 (see FIG. 7), the wire 90u and the one side 60u are pulled, and the wire 90d and the other side 60d are relaxed. The bending portion 2w is bent in a lower direction when the wire 90u and the one side 60u are relaxed, and the wire 90d and the other side 60d are pulled.

In this case, the vertical bending chain member 60 is slidable relative to the surface 70i of the second chain cover 70.

Note that on the surface 70i of the one side 70e of the second chain cover 70, the one side 60u of the vertical bending chain member 60 can slide back and forth in the insertion direction S in an insertion path 50u (see FIG. 4) described later. On the surface 70i of the other side 70f, the other side 60d of the vertical bending chain member 60 can slide back and forth in the insertion direction S in an insertion path 50d (see FIG. 4) described later.

Note that the surface 70i of the one side 70e is exposed to the insertion path 50u, and this will be described later. The surface 70i of the other side 70f is exposed to the insertion path 50d, and this will be described later.

On the surfaces 70i of the one side 70e and the other side 70f of the second chain cover 70, ribs 74 and 75 are formed in the insertion direction S as shown in FIG. 4 on end portions parallel in the insertion direction S, or more specifically, on end portions surrounding the slit 79 and end portions outside in the width direction B.

The rib 74 is formed in a U shape. The rib 74 guides the one side 60u of the vertical bending chain member 60 to prevent the one side 60u from dropping out from the surface 70i of the one side 70e toward the slit 79 and guides the other side 60d of the vertical bending chain member 60 back and forth in the insertion direction S to prevent the other side 60d from dropping out from the surface 70i of the other side 70f toward the slit 79.

The rib 75 guides the one side 60u of the vertical bending chain member 60 to prevent the one side 60u from dropping out from the surface 70i of the one side 70e to the outside in the width direction B and guides the other side 60*d* of the vertical bending chain member 60 back and forth in the insertion direction S to prevent the other side 60*d* from dropping out from the surface 70*i* of the other side 70*f* to the outside in the width direction B.

That is, the ribs 74 and 75 guide the one side 60*u* and the other side 60*d* back and forth in the insertion direction S to prevent the one side 60*u* and the other side 60*d*, or more specifically, at least the connection piece 61 and the connection piece 62, from dropping out from the respective insertion paths 50*u* and 50*d*.

On the surface 70*i* of the second chain cover 70, an alignment convex portion not shown is provided in front of and near the holding hole 78. The alignment convex portion guides the one side 60*u* of the vertical bending chain member 60 to the insertion path 50*u*, that is, the surface 70*i* of the one side 70*e* of the second chain cover 70 and guides the other side 60*d* of the vertical bending chain member 60 to the insertion path 50*d*, that is, the surface 70*i* of the other side 70*f* of the second chain cover 70. The alignment convex portion also prevents interference of the one side 60*u* and the other side 60*d* caused by looseness of one of the one side 60*u* and the other side 60*d*.

The second chain cover 70 is placed on the second surface 50*t* described later of the chain separator 50 to cover the second surface 50*t* to thereby prevent the vertical bending chain member 60, the connection piece 61, and the connection piece 62 from dropping out from the chain separator 50 to the side away from the opposite side of the first surface 50*i* from the second surface 50*t* in the height direction H.

Note that shapes of the first surface 70*t* and the second surface 70*i* of the second chain cover 70 are different, and the operator does not make a mistake in the direction of attaching the second chain cover 70 during the assembly.

The first chain cover 30 and the second chain cover 70 may be formed in a same shape. That is, the first chain cover 30 and the second chain cover 70 may be formed as same members.

That is, the one side 30*e*, the other side 30*f*, the positioning hole 32, the ribs 34 and 35, the alignment convex portion 33, and the holding hole 38 of the first chain cover 30 are equivalent to the other side 70*f*, the one side 70*e*, the positioning hole 72, the ribs 74 and 75, the alignment convex portion not shown, and the holding hole 78 of the second chain cover 70, respectively. The surface 30*i* of the first chain cover 30 is equivalent to the surface 70*t* on the opposite side of the surface 70*i* of the second chain cover 70, and the surface 30*t* is equivalent to the surface 70*i*.

In other words, the first chain cover 30 may be placed on the second surface 50*t* in a state in which the surface 30*i* comes into contact with the second surface 50*t* of the chain separator 50, a distal end of the other side 30*f* is engaged with the engagement portion 59*e*, and a distal end of the one side 30*e* is engaged with the engagement portion 59*f*.

The second chain cover 70 may be arranged between the chain separator 50 and the frame body 20 such that the surface 70*t* faces toward the frame body 20, and the surface 70*i* faces toward the chain separator 50 in the height direction H.

The chain separator 50 configured to guide the back and forth movement of the horizontal bending chain member 40 and the vertical bending chain member 60 in the insertion direction S in the operation portion 3 is fixed on the surface 20*t* of the frame body 20 so as to sandwich the first chain cover 30 between the surface 20*t* and the chain separator 50.

The chain separator 50 is formed from a highly lubricant resin, such as polyacetal (POM), and includes a columnar portion 51, a thin-plate region 56, and a wall portion 57 as shown in FIG. 5.

Note that the columnar portion 51, the thin-plate region 56, and the wall portion 57 are integrally formed. Two positioning protrusions 52 into which the positioning holes 72 of the second chain cover 70 are fitted are formed at one location in the intermediate position in the insertion direction S on the second surface 50*t* of the chain separator 50 closer to the second chain cover 70.

If the second chain cover 70 is formed from a metallic material, and the chain separator 50 is formed by a resin, coefficients of linear expansion of the second chain cover 70 and the chain separator 50 are significantly different.

Therefore, when the coefficients of linear expansion of two members are significantly different, the amounts of deformation under the high-temperature high-humidity environment and under the low-temperature low-humidity environment are different in the second chain cover 70 and the chain separator 50, and the chain separator 50 is deformed during cleaning, disinfection, and sterilization of the endoscope 1 as described above.

If the chain separator 50 is significantly deformed, slidability of the horizontal bending chain member 40 and the vertical bending chain member 60 in the respective insertion paths 50*u*, 50*d*, 50*r*, and 50*l* described later decreases because the chain separator 50 is a member configured to guide the back and forth movement of the horizontal bending chain member 40 and the vertical bending chain member 60 in the insertion direction S as described above, and a bending operation of the bending portion 2*w* is adversely affected.

Even a slight deformation of the chain separator 50 may generate internal stress in the chain separator 50, and for example, when a cleaning/disinfecting apparatus is used to clean and disinfect the endoscope 1, the chain separator 50 is placed under an environment in which a high temperature and a low temperature are repeated. In this case, the internal stress generated in the chain separator 50 may reduce a lifetime of the chain separator 50. Note that the problem can be ignored when the chain separator 50 and the second chain cover 70 are formed by a same material.

Therefore, in the present embodiment, the positioning of the second chain cover 70 relative to the chain separator 50 in the insertion direction S and the width direction B is performed only by fitting the two positioning protrusions 52 provided at only one location in the intermediate position on the second surface 50*t* of the chain separator 50 in the insertion direction S, into the two positioning holes 72 of the second chain cover 70.

Note that other than the fact that the two positioning protrusions 52 are fitted into the two positioning holes 72, the proximal end 70*k* is fixed, and the distal ends 70*es* and 70*fs* are engaged with the engagement portions 59*e* and 59*f*, the second chain cover 70 is just placed such that the surface 70*i* comes into contact with the second surface 50*t*.

As a result, even if the amounts of deformation of the second chain cover 70 and the chain separator 50 are different, since the second chain cover 70 and the chain separator 50 are not tightly joined and fixed, the internal stress generated in the chain separator 50 due to the fixation with the second chain cover 70 can be small, and a large deformation of the chain separator 50 can be eliminated.

Note that the foregoing is the same when the second chain cover 70 is formed from a resin, and the chain separator 50 is formed from metal.

Returning to FIG. 5, a front half portion of the thin-plate region 56 in the insertion direction S is formed into two parts just like the first chain cover 30 and the second chain cover 70 described above, and one side 56e and the other side 56f in the width direction B are fixed in the insertion direction S to center portions in the height direction H on both side surfaces of the columnar portion 51 in the width direction B.

Note that a surface 56i of the thin-plate region 56 closer to the first chain cover 30 faces the surface 30t of the first chain cover 30, and a surface 56t of the thin-plate region 56 closer to the second chain cover 70 faces the surface 70i of the second chain cover 70.

A center portion of the wall portion 57 in the height direction H is fixed to a circumference end portion so as to cover the circumference end portion except the surface 56i and the surface 56t on a proximal end side of the thin-plate region 56.

An end portion of the wall portion 57 closer to the first surface 50i is a surface coming into contact with the surface 20t of the frame body 20, and an end portion closer to the second surface 50t is a surface coming into contact with the surface 70i of the second chain cover 70.

Note that the wall portion 57 has a function of preventing the horizontal bending chain member 40 wound around the winding portion 45m of the sprocket 45 from dropping outside of the chain separator 50 from a proximal end side of the surface 56i of the thin-plate region 56 and preventing the vertical bending chain member 60 wound around the winding portion 65m of the sprocket 65 from dropping outside of the chain separator 50 from a proximal end side of the surface 56t of the thin-plate region 56.

A holding hole 58 of the sprockets 45 and 65 penetrating in the height direction H is formed on the proximal end side of the thin-plate region 56. The sprocket 45 is fitted to the holding hole 58 and the holding hole 38, and the sprocket 45 is pivotably held on the side of the surface 56i of the thin-plate region 56. The sprocket 65 is fitted to the holding hole 58 and the holding hole 78, and the sprocket 65 is pivotably held on the side of the surface 56t of the thin-plate region 56.

On the surface 56i of the thin-plate region, an alignment convex portion not shown is provided in front of and near the holding hole 58. The alignment convex portion guides the one side 40r of the horizontal bending chain member 40 to the insertion path 50r described later and guides the other side 40l of the horizontal bending chain member 40 to the insertion path 50l described later. Along with the alignment convex portion 33 of the first chain cover 30, the alignment convex portion also prevents interference of the one side 40r and the other side 40l caused by looseness of one of the one side 40r and the other side 40l.

On the surface 56t of the thin-plate region, an alignment convex portion 53t is provided in front of and near the holding hole 58. The alignment convex portion 53t guides the one side 60u of the vertical bending chain member 60 to the insertion path 50u described later and guides the other side 60d of the vertical bending chain member 60 to the insertion path 50d described later. Along with the alignment convex portion of the second chain cover 70, the alignment convex portion 53t also prevents interference of the one side 60u and the other side 60d caused by looseness of one of the one side 60u and the other side 60d.

The columnar portion 51 internally includes a space 51k opening upward in the height direction H in FIGS. 2, 3, 5, and 6 to 9. The link mechanism 130 described above is fitted to the space 51k through the slit 79 of the second chain cover 70 as shown in FIG. 3.

The columnar portion 51 comes into contact with the surface 20t of the frame body 20 through the slit 39 of the first chain cover 30.

The engagement protrusions 50w protruding forward are formed on a distal end of the columnar portion 51. The engagement protrusions 50w are engaged with the respective engagement grooves 25t of the two support members 25e and 25f rising up from the surface 20t of the frame body 20. The chain separator 50 is fixed to the surface 20t by screws or the like in a state that the distal end of the chain separator 50 is positioned by engaging the engagement protrusions 50w with the engagement grooves 25t.

As shown in FIG. 4, along with the surface 30t of the one side 30e of the first chain cover 30, a side surface 51r closer to the first surface 50i than the one side 56e of the thin-plate region 56 in the columnar portion 51 and a surface 56r forming the surface 56i of the one side 56e form, on the chain separator 50, the insertion path 50r in which the one side 40r and the connection piece 41 of the horizontal bending chain member 40 are inserted.

Along with the second surface 30t of the other side 30f of the first chain cover 30, a side surface 51l closer to the first surface 50i than the other side 56f of the thin-plate region 56 in the columnar portion 51 and a surface 56l forming the surface 56i of the other side 56f form, on the chain separator 50, the insertion path 50l in which the other side 40l and the connection piece 42 of the horizontal bending chain member 40 are inserted.

Along with the surface 70i of the one side 70e of the second chain cover 70, a side surface 51u closer to the second surface 50t than the one side 56e of the thin-plate region 56 in the columnar portion 51 and a surface 56u forming the surface 56t of the one side 56e form, on the chain separator 50, the insertion path 50u in which the one side 60u and the connection piece 61 of the vertical bending chain member 60 are inserted.

Along with the surface 70i of the other side 70f of the second chain cover 70, a side surface 51d closer to the second surface 50t than the other side 56f of the thin-plate region 56 in the columnar portion 51 and a surface 56d forming the surface 56t of the other side 56f form, on the chain separator 50, the insertion path 50d in which the other side 60d and the connection piece 62 of the vertical bending chain member 60 are inserted.

In this way, the chain separator 50 has a function of separately arranging the horizontal bending chain member 40 and the vertical bending chain member 60 and guiding the movement of the horizontal bending chain member 40 and the vertical bending chain member 60.

Note that the insertion path 50r and the insertion path 50u are separately positioned to overlap in the height direction H across the one side 56e of the thin-plate region 56. Therefore, the one side 40r and the connection piece 41 of the horizontal bending chain member 40 and the one side 60u and the connection piece 61 of the vertical bending chain member 60 are separately positioned and overlap in the height direction H across the one side 56e of the thin-plate region 56.

The insertion path 50l and the insertion path 50d are separately positioned and overlap in the height direction H across the other side 56f of the thin-plate region 56. Therefore, the other side 40l and the connection piece 42 of the horizontal bending chain member 40 and the other side 60d and the connection piece 62 of the vertical bending chain member 60 are separately positioned and overlap in the height direction H across the other side 56f of the thin-plate region 56.

The insertion path 50r and the insertion path 50l are separately positioned and overlap in the width direction B through the columnar portion 51, and similarly, the insertion path 50u and the insertion path 50d are separately positioned and overlap in the width direction B through the columnar portion 51.

A rib 55r is formed on an end portion outside of the surface 56r of the thin-plate region 56 in the width direction B to guide, along with the rib 35, the one side 40r and the connection piece 41 of the horizontal bending chain member 40 to prevent the one side 40r and the connection piece 41 from dropping out to the outside in the width direction B from the surface 56r, that is, to guide the one side 40r and the connection piece 41 back and forth in the insertion direction S to prevent the one side 40r and the connection piece 41 from dropping out from the insertion path 50r.

A rib 55l is formed on an end portion outside of the surface 56l of the thin-plate region 56 in the width direction B to guide, along with the rib 35, the other side 40l and the connection piece 42 of the horizontal bending chain member 40 to prevent the other side 40l and the connection piece 42 from dropping out to the outside in the width direction B from the surface 56l, that is, to guide the other side 40l and the connection piece 42 back and forth in the insertion direction S to prevent the other side 40l and the connection piece 42 from dropping out from the insertion path 50l.

A rib 55u is formed on an end portion outside of the surface 56u of the thin-plate region 56 in the width direction B to guide, along with the rib 75, the one side 60u and the connection piece 61 of the vertical bending chain member 60 to prevent the one side 60u and the connection piece 61 from dropping out to the outside in the width direction B from the surface 56u, that is, to guide the one side 60u and the connection piece 61 back and forth in the insertion direction S to prevent the one side 60u and the connection piece 61 from dropping out from the insertion path 50u.

A rib 55d is formed on an end portion outside of the surface 56d of the thin-plate region 56 in the width direction B to guide, along with the rib 75, the other side 60d and the connection piece 62 of the vertical bending chain member 60 to prevent the other side 60d and the connection piece 62 from dropping out to the outside in the width direction B from the surface 56d, that is, to guide the other side 60d and the connection piece 62 back and forth in the insertion direction S to prevent the other side 60d and the connection piece 62 from dropping out from the insertion path 50d.

As shown in FIGS. 2, 3, 5, and 6, the engagement protrusions 50w protruding forward are formed on the distal end of the columnar portion 51.

The engagement protrusions 50w are engaged with the respective engagement grooves 25t of the two support members 25e and 25f rising up from the surface 20t of the frame body 20. The chain separator 50 is fixed to the surface 20t by screws or the like in a state that the distal end of the chain separator 50 is positioned by engaging the engagement protrusions 50w with the engagement grooves 25t.

As shown in FIGS. 2, 3, and 5 to 9, the engagement portion 59e in an L shape in which the distal end 70es of the one side 70e of the second chain cover 70 is engaged and the engagement portion 59f in an L shape in which the distal end 70fs of the other side 70f of the second chain cover 70 is engaged are provided at positions closer to the second surface 50t at the distal end of the columnar portion 51.

Note that the engagement portions 59e and 59f may be formed in a U shape including holes into which the distal ends 70es and 70fs are fitted, respectively.

As shown in FIG. 8, the surfaces 70t of the distal ends 70es and 70fs are engaged with surfaces 59ei and 59fi on sides facing the frame body 20 in the height direction H, respectively, and the engagement portions 59e and 59f form restriction surfaces for restricting the movement of the second chain cover 70 in the height direction H from the second surface 50t toward the opposite side of the first surface 50i.

Note that as shown in FIG. 9, the second surface 50t of the chain separator 50 forms a restriction surface for restricting the movement of the second chain cover 70 in the height direction H toward the first surface 50i, by the surface 70i of the second chain cover 70 coming into contact therewith.

Thus, the positioning protrusions 52 are fitted into the positioning holes 72, and the position of the second chain cover 70 in the insertion direction S and the width direction B relative to the chain separator 50 is defined in the present embodiment. In the state that the proximal end 70k is fixed to the frame body 20 by the frame shaft 99, and the distal ends 70es and 70fs are engaged with the engagement portions 59e and 59f of the chain separator 50, the second chain cover 70 is placed on the second surface 50t of the chain separator 50.

That is, the second chain cover 70 can be easily and simply positioned, placed, and fixed on the second surface 50t without using screws or the like in the present embodiment.

Note that although not shown, an engagement portion in which the distal end of the one side 30e of the first chain cover 30 is engaged and an engagement portion in which the distal end of the other side 30f of the first chain cover 30 is engaged may be provided at a position on the distal end of the columnar portion 51 closer to the first surface 50i.

In this case, the respective distal ends of the one side 30e and the other side 30f are engaged with the respective engagement portions, and the respective engagement portions form a restriction surface for restricting the movement of the first chain cover 30 toward the frame body 20 in the height direction H. The first surface 50i of the chain separator 50 forms a restriction surface for restricting movement of the first chain cover 30 from the first surface 50i toward the second surface 50t in the height direction H, by the surface 30t of the first chain cover 30 coming into contact therewith.

Therefore, in this case, the first chain cover 30 can be easily and simply positioned, placed, and fixed on the first surface 50i without using screws or the like, just like the second chain cover 70.

Here, as described above, the second chain cover 70 is formed from a resin. Therefore, in the state in which the proximal end 70k is fixed, and the distal ends 70es and 70fs are engaged with the engagement portions 59e and 59f, the center portion in the insertion direction S may be deflected by weights of the one side 60u and the connection piece 61 of the vertical bending chain member 60 as well as the other side 60d and the connection piece 62 of the vertical bending chain member 60 inserted into the insertion paths 50u and 50d when a posture of the operation portion 3 is changed such that the second chain cover 70 is positioned on a lower side in a direction of gravity.

Note that in the configuration in which the respective distal ends of the one side 30e and the other side 30f of the first chain cover 30 are engaged with engagement portions provided on the distal end of the columnar portion 51 of the chain separator 50, the first chain cover 30 is placed between the frame body 20 and the chain separator 50 in the height direction. Therefore, even when the first chain cover 30 is formed from a resin, the first chain cover 30 is not deflected by the weights of the one side 40r and the connection piece 41 of the horizontal bending chain member 40 as well as the other side 40l and the connection piece 42 of the horizontal bending chain member 40 inserted into the insertion paths 50r and 50l even if the frame body 20 formed from a metallic material changes the posture of the operation portion 3 such that the first chain cover 30 is positioned on the lower side in the direction of gravity.

However, when the first chain cover 30 is placed and fixed on the first surface 50i of the chain separator 50 before the first chain cover 30 is assembled on the frame body 20, a fixation structure is the same as when the second chain cover 70 is placed and fixed on the second surface 50t of the chain separator 50. Therefore, there is the problem that the first chain cover 30 is deflected.

Thus, in the present embodiment, guide blocks 88f and 88e for preventing the vertical bending chain member 60, the connection pieces 61 and 62, the horizontal bending chain member 40, and the connection pieces 41 and 42 from dropping out from the chain separator 50 to the outside in the width direction B and for preventing the deflection of the first chain cover 30 and the second chain cover 70 in the height direction caused by the weights of the vertical bending chain member 60, the connection pieces 61 and 62, the horizontal bending chain member 40, and the connection pieces 41 and 42 are fixed to both side surfaces, respectively, of the bending operation apparatus 100 in the width direction B, or more specifically, both side surfaces of the chain separator 50, the first chain cover 30, and the second chain cover 70 in the width direction B, as shown in FIGS. 5 and 6.

More specifically, sandwiching portions 88fk and 88ek for sandwiching the chain separator 50, the first chain cover 30, and the second chain cover 70 in the height direction H are provided at upper side and lower side of the guide blocks 88f and 88e in the height direction H, respectively.

The respective sandwiching portions 88fk and 88ek sandwich the chain separator 50, the first chain cover 30, and the second chain cover 70 in the height direction H, and the guide blocks 88f and 88e prevent deflection of the first chain cover 30 and the second chain cover 70 in the height direction.

The guide blocks 88f and 88e block both side surfaces of the chain separator 50, the first chain cover 30, and the second chain cover 70 in the width direction B to prevent the vertical bending chain member 60, the connection pieces 61 and 62, the horizontal bending chain member 40, and the connection pieces 41 and 42 from dropping out from the chain separator 50 to the outside in the width direction B.

Note that through holes 89fv and 89ev formed on the bearing plates 89f and 89e fitted to the respective guide blocks 88f and 88e are aligned with the screw holes 20v of the frame body 20, and then the screws inserted into the through holes 89fv and 89ev are screwed to the screw holes 20v to fix the guide blocks 88f and 88e to the frame body 20.

The guide blocks 88f and 88e also have a function of adjusting a maximum bending angle of the bending portion 2w. The connection pieces 41, 42, 61, and 62 for moving the insertion paths 50u, 50d, 50r, and 50l back and forth in the insertion direction S are caught at setting positions in the insertion direction S on surfaces facing the both end surfaces of the chain separator 50 in the width direction B, and amounts of movement of the vertical bending chain member 60, the horizontal bending chain member 40, and the wires 90u, 90d, 90r, and 90l in the insertion direction S are adjusted.

Note that to assemble the frame body 20, the first chain cover 30, the sprocket 45, the horizontal bending chain member 40, the chain separator 50, the sprocket 65, the vertical bending chain member 60, the second chain cover 70, and the guide blocks 88f and 88e shown in FIG. 5, the positioning holes 32 of the first chain cover 30 are first fitted into the positioning protrusions 22 of the frame body 20, and the first chain cover 30 is positioned on the frame body 20. In this state, the surface 30i of the first chain cover 30 is brought into contact with the surface 20t of the frame body 20.

Subsequently, the sprocket 45 is engaged with the holding hole 38 of the first chain cover 30, and the intermediate position of the horizontal bending chain member 40 is wound around the winding portion 45m of the sprocket 45 to thereby place the horizontal bending chain member 40 on the surface 30t of the first chain cover 30.

In this case, the one side 40r and the connection piece 41 of the horizontal bending chain member 40 are placed on the surface 30t of the one side 30e of the first chain cover 30, and the other side 40l and the connection piece 42 are placed on the surface 30t of the other side 30f.

Subsequently, the engagement protrusions 50w provided at the distal end of the chain separator 50 are engaged with the respective engagement grooves 25t of the two support members 25e and 25f rising up from the surface 20t of the frame body 20, and the columnar portion 51 of the chain separator 50 is brought into contact with the surface 20t of the frame body 20 through the slit 39 of the first chain cover 30. The one side 40r and the connection pieces 41 as well as the other side 40l and the connection piece 42 of the horizontal bending chain member 40 are inserted into the respective insertion paths 50r and 50l, and the chain separator 50 is fixed to the surface 20t of the frame body 20 to hold the sprocket 45 by the holding hole 58.

Next, the sprocket 65 is engaged with the holding hole 58 of the chain separator 50, and the intermediate position of the vertical bending chain member 60 is wound around the winding portion 65m of the sprocket 65 to thereby place the vertical bending chain member 60 on the surface 56t of the thin-plate region 56 of the chain separator 50.

In this case, the one side 60u and the connection piece 61 of the vertical bending chain member 60 are placed on the surface 56u forming the surface 56t of the one side 56e of the thin-plate region 56, and the other side 60d and the connection piece 62 are placed on the surface 56d forming the surface 56t of the other side 56f of the thin-plate region 56.

Next, the positioning holes 72 of the second chain cover 70 are fitted into the positioning protrusions 52 of the chain separator 50, engage the sprocket 65 with the holding hole 78 of the second chain cover 70, and the surface 70i of the second chain cover 70 is brought into contact with the second surface 50t of the chain separator 50 in a state that the second chain cover 70 is positioned relative to the chain separator 50.

Subsequently, the distal end 70es of the one side 70e and the distal end 70fs of the other side 70f of the second chain cover 70 are engaged with the engagement portions 59e and 59f, respectively, at the distal end of the columnar portion 51 of the chain separator 50.

Note that in this state, the positioning protrusions 52 of the chain separator 50 are fitted into the positioning holes 72, and the distal ends 70es and 70fs are engaged with the engagement portions 59e and 59f in the second chain cover 70. In this way, the engagement portions 59e and 59f form a restriction surface restricting the movement of the second chain cover 70 from the second surface 50t toward the opposite side of the first surface 50i in the height direction H, and the second surface 50t of the chain separator 50 forms a restriction surface restricting the movement of the second chain cover 70 toward the first surface 50i in the height direction H as described above. Therefore, even when the proximal end 70k of the second chain cover 70 is not fixed, the second chain cover 70 does not drop out from the second surface 50t.

Next, the frame shaft 99 is used to press the proximal end 70k of the second chain cover 70 against the surface 20t along with the proximal end of the chain separator 50 and the proximal end 30k of the first chain cover 30. Subsequently, a region coming into contact with the surface 20t of the frame shaft 99 is fixed to the frame body 20 by the screw 98.

As a result, the one side 60u and the connection piece 61 as well as the other side 60d and the connection piece 62 of the vertical bending chain member 60 are inserted into the respective insertion paths 50u and 50d.

Lastly, the both side surfaces of the chain separator 50, the first chain cover 30, and the second chain cover 70 in the width direction B are blocked by the guide blocks 88f and 88e, and the bearing plates 89f and 89e fitted to the guide blocks are fixed to the frame body 20 by screws to assemble part of the bending operation apparatus 100.

In this way, at least the second chain cover 70 is placed and fixed to the second surface 50t of the chain separator 50 only by fitting the positioning protrusions 52 into the positioning holes 72 and engaging the distal end 70es of the one side 70e and the distal end 70fs of the other side 70f with the engagement portions 59e and 59f at the distal end of the columnar portion 51 of the chain separator 50 in the state that the proximal end 70k is fixed to the frame body 20 in the present embodiment.

According to this, the second chain cover 70 can be simply positioned and fixed on the second surface 50t, that is, on the frame body 20 along with the chain separator 50 and the first chain cover 30, without using screws or the like as in the conventional technique.

Since the screws are not used, the second chain cover 70 is not collapsed, cracked, or deformed by screwing even when the second chain cover 70 is formed from a resin, and the weight of the operation portion does not increase.

Note that the effects are the same in a configuration in which respective distal ends of the one side 30e and the other side 30f of the first chain cover 30 are engaged with the engagement portions of the chain separator 50.

Thus, an operation mechanism of insertion device and an insertion device can be provided, in which the weight can be reduced, and the chain covers 30 and 70 can be simply fixed to the frame body 20 along with the chain separator 50.

Note that a modification will be illustrated below with reference to FIGS. 10 and 11.

Figure 10:
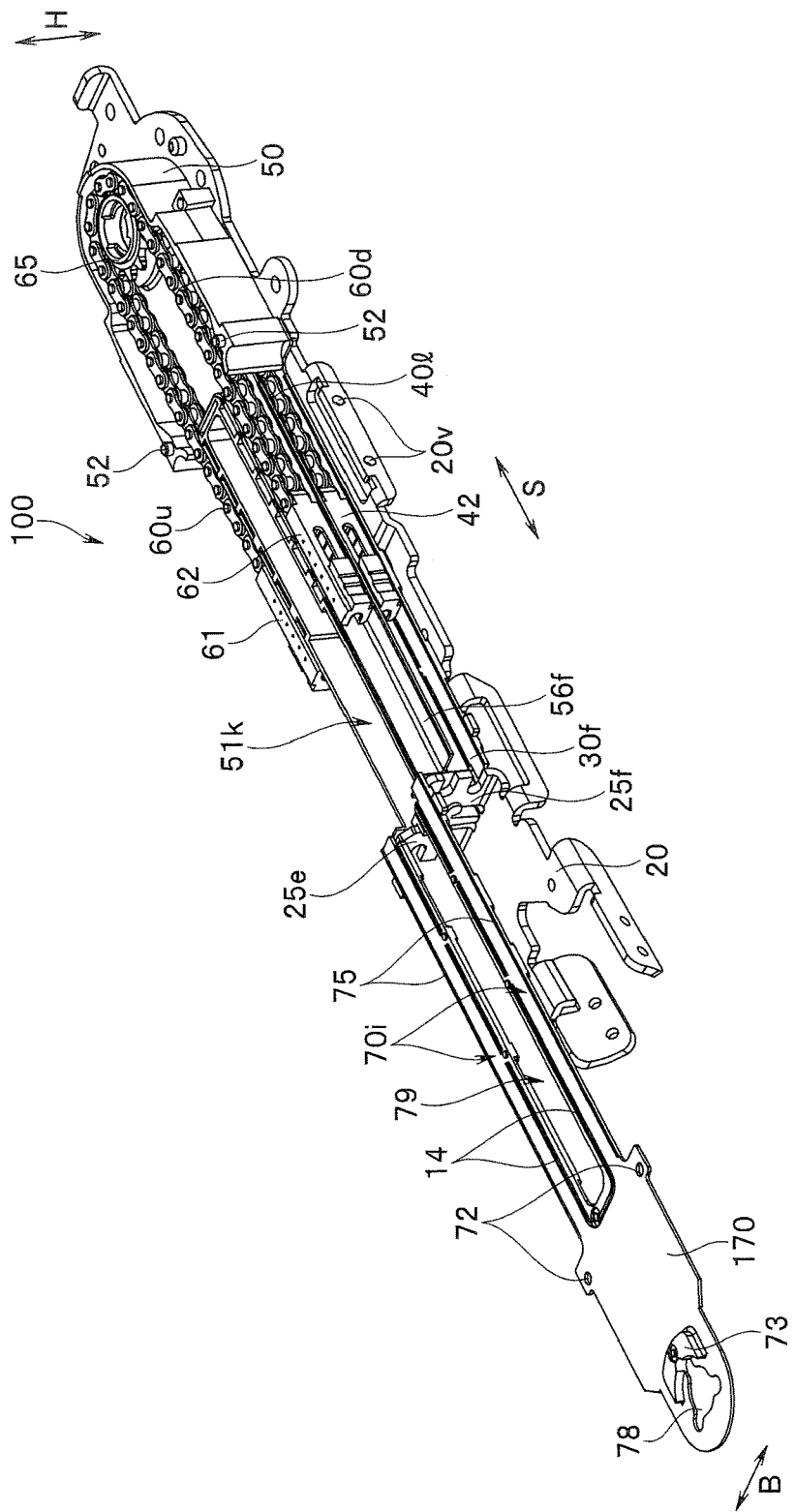
FIG. 10 is a perspective view illustrating a modification of forming the second chain cover integrally with the chain separator in a configuration of the bending operation apparatus of FIG. 5.

FIG. 10 is a perspective view showing a modification of forming the second chain cover integrally with the chain separator in the configuration of the bending operation apparatus of FIG. 5. FIG. 11 is a side view schematically showing a configuration of bending the second chain cover of FIG. 10 by 180° and placing the second chain cover on the second surface of the chain separator.

Figure 11:
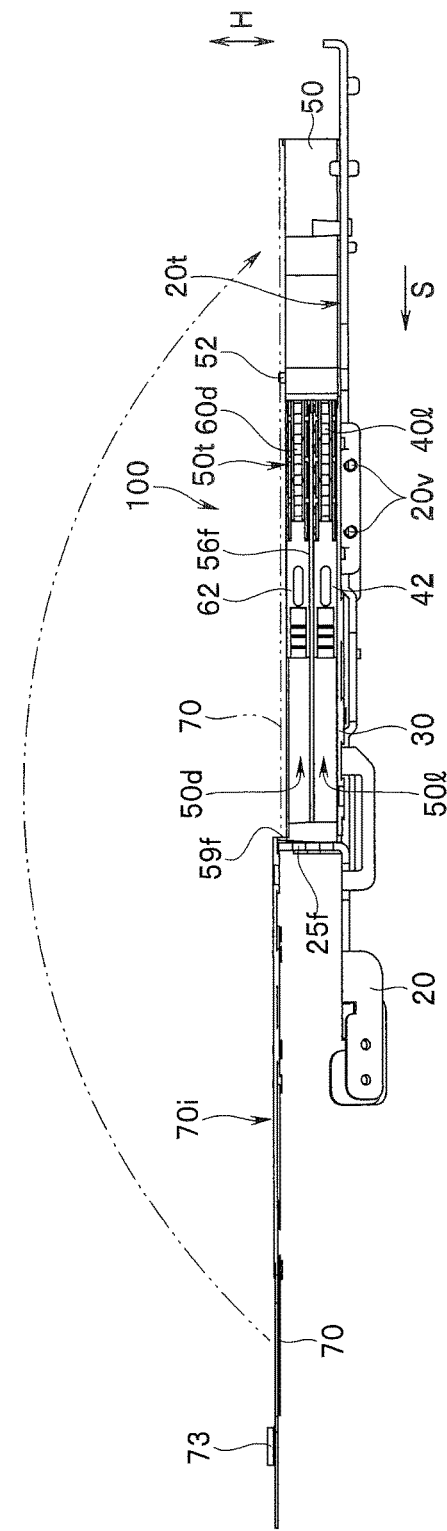
FIG. 11 is a side view schematically showing a configuration of bending a second chain cover of FIG. 10 by 180° and placing the second chain cover on the second surface of the chain separator.

As shown in FIGS. 10 and 11, the second chain cover 70 may be formed integrally with the chain separator 50.

More specifically, the distal end of the second chain cover 70 may be fixed to upper surfaces of the engagement portion 59e and 59f provided at the distal end of the columnar portion 51 such that the distal end can be opened and closed 180°, for example.

Note that the distal end of the second chain cover 70 may be directly fixed to an upper surface of the distal end of the columnar portion 51 instead of the engagement portions 59e and 59f. In the present configuration, the second chain cover 70 is formed from a resin.

Note that as indicated by an alternate long and two short dashes line in FIG. 11, after the second chain cover 70 is folded and closed, the second chain cover 70 is placed on the second surface 50t, and the proximal end 70k of the second chain cover 70 is fixed to the frame body 20 by the frame shaft 99 as in the present embodiment described above.

The assembly of the chain separator 50 relative to the frame body 20 and the assembly of the vertical bending chain member 60, the horizontal bending chain member 40, and the sprockets 45 and 65 in the chain separator 50 are performed in a state that the second chain cover 70 is opened, that is, a state that the second surface 50t of the chain separator 50 is exposed, as shown in FIGS. 10 and 11.

Subsequently, to place the second chain cover 70 on the second surface 50t, the second chain cover 70 protruding and positioned in front of the distal end of the columnar portion 51 is rotated and folded substantially 180° counterclockwise until the surface 70i comes into contact with the second surface 50t as shown in FIGS. 10 and 11.

As a result, the second surface 50t is blocked by the second chain cover 70, and the second chain cover 70 is placed on the second surface 50t as indicated by an alternate long and two short dashes line in FIG. 11.

Note that after the second chain cover is closed, the positioning protrusions 52 are fitted into the positioning holes 72 to position the second chain cover 70 relative to the chain separator 50 as in the present embodiment.

According to the configuration, the second chain cover 70 can be formed integrally with the chain separator 50, and the number of components can be reduced. Furthermore, the distal end of the second chain cover 70 does not have to be engaged as in the present embodiment described above, and the second chain cover 70 can be placed and fixed on the second surface 50t more simply than in the present embodiment just by rotating and folding the second chain cover 70 in the open state substantially 180° counterclockwise about the distal end of the second chain cover 70.

Note that the other effects are the same as in the present embodiment described above.

In the example of the configuration illustrated in the present embodiment, four insertion paths 50r, 50l, 50u, and 50d for first long members and second long members are formed on the chain separator 50. The arrangement is not limited to this, and only two insertion paths for first long members may be formed on the chain separator 50 when the bending portion 2w is bent only in two directions.

Although the insertion device is the endoscope 1 in the example illustrated in the present embodiment, the insertion device is not limited to this. The insertion device can also be applied to other insertion devices including bending portions and other action portions in the insertion portions. That is, the operation mechanism of the insertion device according to the present embodiment can also be applied to an operation mechanism of an insertion device other than the endoscope.

What is claimed is:

1. An endoscope comprising:
  a bendable bending portion provided on an insertion portion inserted into a subject;

an operation portion consecutively connected to a proximal end of the insertion portion, the operation portion being operated by an operator to bend the bending portion;

a frame body fixed in the operation portion;

a first elongated member connected to the bending portion, inserted into the insertion portion and the operation portion, and moved by operating the operation portion;

a second elongated member connected to the bending portion, inserted into the insertion portion and the operation portion, and moved by operating the operation portion;

a guide member configured to separately arrange the first elongated member and the second elongated member and guide the movement of the first elongated member along with the frame body;

a first plate-like member arranged to face the guide member to guide the second elongated member along with the guide member; and an engagement portion formed on the guide member and including a restriction surface for restricting movement of the first plate-like member in a direction away from the guide member, the restriction surface causing the first plate-like member to engage with the guide member.

2. The endoscope according to claim 1, wherein
the guide member includes a first surface and a second surface on an opposite side of the first surface, the first surface being arranged to face the frame body,
the first plate-like member is arranged to face the second surface of the guide member, and
the restriction surface restricts movement of the first plate-like member from the second surface of the guide member toward the opposite side of the first surface.

3. The endoscope according to claim 2, wherein the engagement portion is formed in an L shape, and the restriction surface is formed as a surface on a side facing the frame body.

4. The endoscope according to claim 1, further comprising a second plate-like member placed between the frame body and a first surface of the guide member facing the frame body in the operation portion, the second plate-like member being configured to guide movement of the first elongated member and prevent the first elongated member from dropping out from the guide member toward the frame body.

5. The endoscope according to claim 4, wherein the first plate-like member guides movement of the second elongated member placed on a second surface on an opposite side of the first surface of the guide member in the operation portion and prevents the second elongated member from dropping out from the guide member toward a side away from the second surface on the opposite side of the first surface.

6. The endoscope according to claim 5, wherein each proximal end of the first plate-like member and the second plate-like member in an insertion direction of the insertion portion is fixed to the frame body.

7. The endoscope according to claim 6, wherein a distal end of the second plate-like member in the insertion direction is further engaged with the engagement portion.

8. The endoscope according to claim 7, wherein
the first surface forms a restriction surface for restricting movement of the second plate-like member toward the second surface, and
the engagement portion forms a restriction surface for restricting movement of the second plate-like member toward the frame body.

9. The endoscope according to claim 6, wherein positioning protrusions fitted into positioning holes formed on the first plate-like member and the second plate-like member to position the first plate-like member and the second plate-like member relative to the guide member in the insertion direction and in a width direction orthogonal to the insertion direction and a height direction connecting the first surface and the second surface are provided at one location of an intermediate position of the first surface and the second surface in the insertion direction.

10. The endoscope according to claim 6, wherein on both side surfaces of the guide member, the first plate-like member, and the second plate-like member in a width direction orthogonal to the insertion direction and a height direction connecting the first surface and the second surface, guide blocks configured to prevent the first elongated member and the second elongated member from dropping out in the width direction from the guide member and prevent deflection of the first plate-like member and the second plate-like member in the height direction due to weights of the first elongated member and the second elongated member are fixed to the frame body.

11. The endoscope according to claim 10, wherein sandwiching portions configured to sandwich the guide member, the first plate-like member, and the second plate-like member in the height direction are provided on the guide blocks.

12. The endoscope according to claim 5, wherein
the first plate-like member and the second plate-like member are formed in a same shape, and
a surface of the first plate-like member on an opposite side of a surface on which the second plate-like member is placed on the first surface is placed on the second surface.

13. The endoscope according to claim 4, wherein the first plate-like member and the second plate-like member are formed from a resin.

* * * * *